United States Patent [19]

Luther

[11] Patent Number: 5,569,217
[45] Date of Patent: Oct. 29, 1996

[54] PERCUTANEOUS PORT CATHETER ASSEMBLY AND METHOD OF USE

[75] Inventor: Ronald B. Luther, Newport Beach, Calif.

[73] Assignee: Luther Medical Products, Inc., Tustin, Calif.

[21] Appl. No.: 331,222

[22] Filed: Oct. 27, 1994

Related U.S. Application Data

[62] Division of Ser. No. 144,881, Oct. 28, 1993, Pat. No. 5,403,283.

[51] Int. Cl.$^6$ .................... A61M 25/00; A61M 31/00
[52] U.S. Cl. .................... 604/280; 604/51; 604/164; 604/198; 604/263
[58] Field of Search ................ 604/164, 165, 604/198, 280, 263, 51–52

[56] References Cited

U.S. PATENT DOCUMENTS

| | | | |
|---|---|---|---|
| 561,059 | 5/1896 | Mitchell et al. | |
| 3,225,762 | 12/1965 | Guttman | 128/214 |
| 3,352,306 | 11/1967 | Hirsch | 128/214.4 |
| 3,463,152 | 8/1969 | Sorenson | 128/214.4 |
| 3,630,195 | 12/1971 | Santomieri | 128/133 |
| 3,834,380 | 9/1974 | Boyd | 128/133 |
| 4,194,504 | 3/1980 | Harms et al. | 128/214.4 |
| 4,249,541 | 2/1981 | Pratt | 128/753 |
| 4,327,722 | 5/1982 | Groshong et al. | 128/214.4 |
| 4,353,369 | 10/1982 | Muetterties | 128/214.4 |
| 4,392,856 | 7/1983 | Lichtenstein | 604/177 |
| 4,431,426 | 2/1984 | Groshong et al. | 604/280 |
| 4,439,583 | 3/1984 | Gould et al. | 525/127 |
| 4,525,157 | 6/1985 | Vaillancourt | 604/52 |
| 4,529,399 | 7/1985 | Groshong et al. | 604/53 |
| 4,549,879 | 10/1985 | Groshong et al. | 604/247 |
| 4,559,046 | 12/1985 | Groshong et al. | 604/282 |
| 4,588,398 | 5/1986 | Daugherty et al. | 604/265 |
| 4,627,841 | 12/1986 | Dorr | 604/158 |
| 4,668,225 | 5/1987 | Russo et al. | 604/270 |
| 4,671,795 | 6/1987 | Mulchin | 604/281 |
| 4,671,796 | 6/1987 | Groshong et al. | 604/247 |
| 4,690,675 | 9/1987 | Katz | 604/177 |
| 4,701,166 | 10/1987 | Groshong et al. | 604/247 |
| 4,728,322 | 3/1988 | Walker et al. | 604/165 |
| 4,770,655 | 9/1988 | Haber et al. | 604/110 |
| 4,772,264 | 9/1988 | Cragg | 604/158 |
| 4,772,276 | 9/1988 | Wiita et al. | 604/283 |
| 4,773,901 | 9/1988 | Norton | 604/265 |
| 4,798,597 | 1/1989 | Vaillancourt | 604/270 |
| 4,828,549 | 5/1989 | Kvalo | 604/164 |
| 4,846,799 | 7/1989 | Tanaka et al. | 604/158 |
| 4,846,812 | 7/1989 | Walker et al. | 604/264 |
| 4,863,432 | 9/1989 | Kvalo | 604/177 |
| 4,887,998 | 12/1989 | Martin et al. | 604/110 |
| 4,895,564 | 1/1990 | Farrell | 604/164 |
| 4,898,591 | 2/1990 | Jang et al. | 604/282 |
| 4,911,691 | 3/1990 | Aniuk et al. | 604/164 |
| 4,917,671 | 4/1990 | Chang | 604/168 |
| 4,927,415 | 5/1990 | Brodsky | 604/164 |
| 4,944,728 | 7/1990 | Carrell et al. | 604/164 |
| 4,950,252 | 8/1990 | Luther et al. | 604/198 |
| 4,955,863 | 9/1990 | Walker et al. | 604/165 |
| 4,976,704 | 12/1990 | McLees | 604/265 |
| 4,986,814 | 1/1991 | Burney et al. | 604/164 |
| 4,994,046 | 2/1991 | Wesson et al. | 604/198 |
| 4,998,919 | 3/1991 | Schnepp-Pesch | 604/164 |

(List continued on next page.)

FOREIGN PATENT DOCUMENTS

| | | |
|---|---|---|
| 0247590 | 5/1987 | European Pat. Off. |
| WO9007349 | 7/1990 | WIPO |

Primary Examiner—Randall L. Green
Assistant Examiner—A. T. Nguyen
Attorney, Agent, or Firm—Stetina Brunda & Buyan

[57] ABSTRACT

Apparatus and method for introducing a catheter into a surgically implanted port. The apparatus has a housing attached to a stylet, with the stylet being received in a catheter. Also provided in the apparatus is a casing with a protective cap that slidably fits within the housing. Also disclosed is a method of catheterizing a surgically implanted port by means of inserting a styler encased in a catheter and retracting the stylet.

7 Claims, 3 Drawing Sheets

U.S. PATENT DOCUMENTS

| | | | |
|---|---|---|---|
| 5,002,533 | 3/1991 | Jullien | 604/110 |
| 5,026,353 | 6/1991 | Bartman | 604/192 |
| 5,037,402 | 8/1991 | Bartman | 604/198 |
| 5,112,312 | 5/1992 | Luther | 604/177 |
| 5,120,317 | 6/1992 | Luther | 604/158 |
| 5,135,502 | 8/1992 | Koenig, Jr. | 604/164 |
| 5,147,332 | 9/1992 | Moorehead | 604/247 |
| 5,205,829 | 4/1993 | Lituchy | 604/164 |
| 5,273,540 | 12/1993 | Luther et al. | 604/110 |

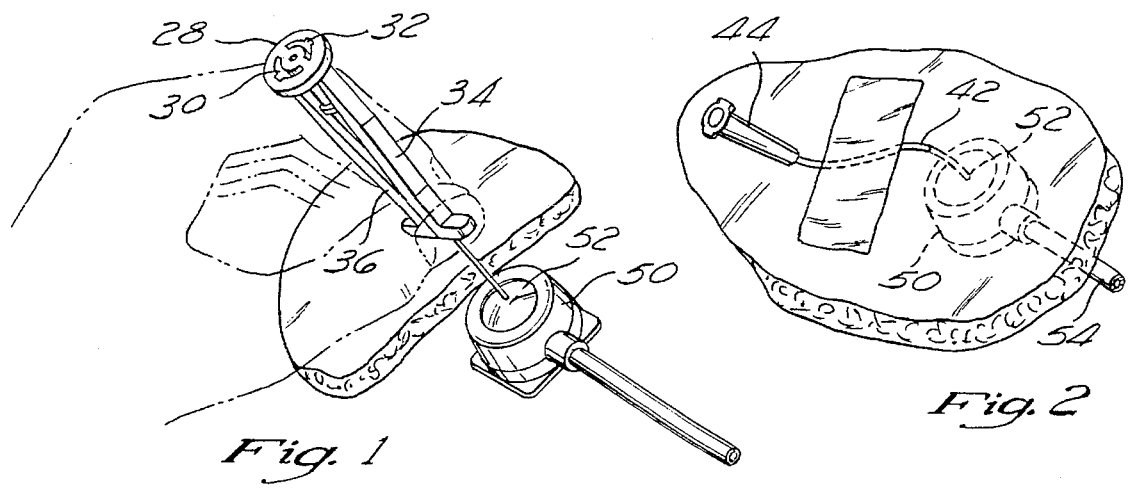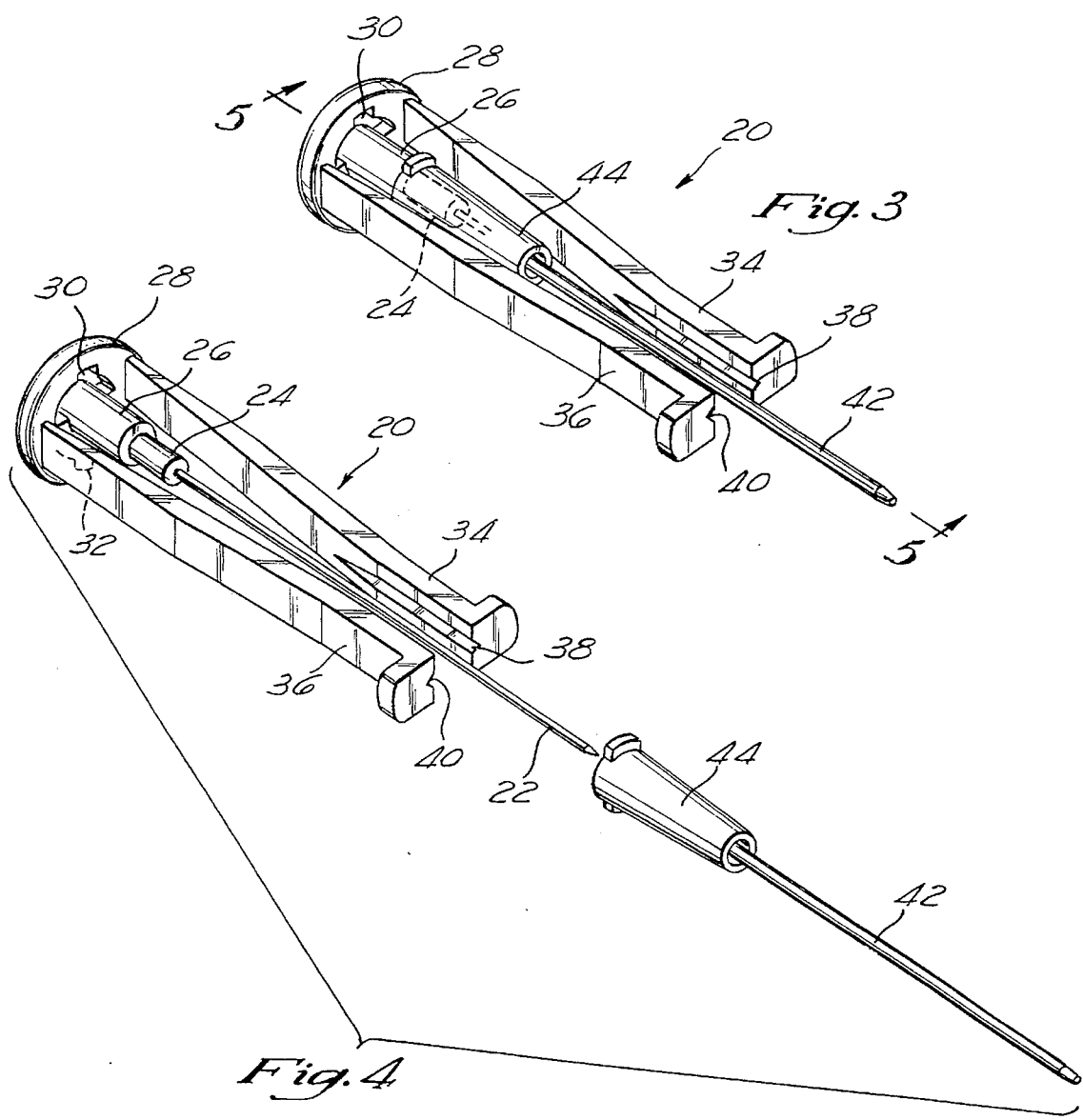

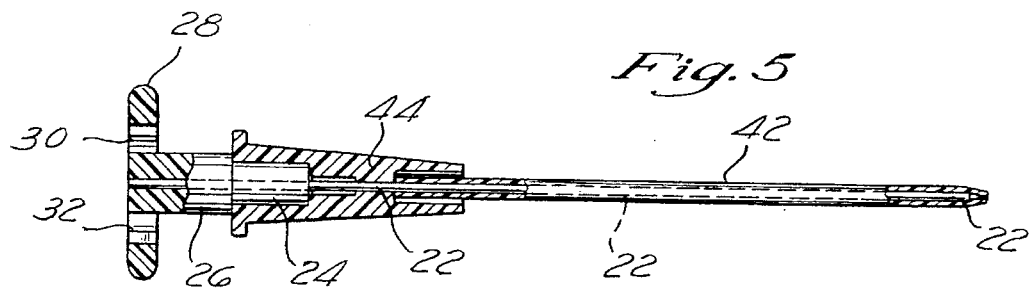
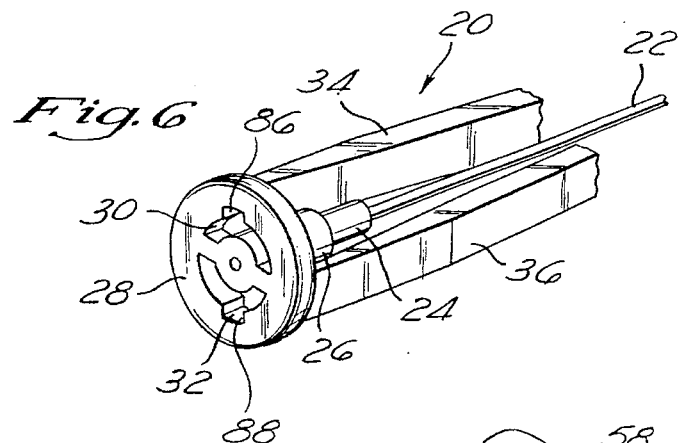
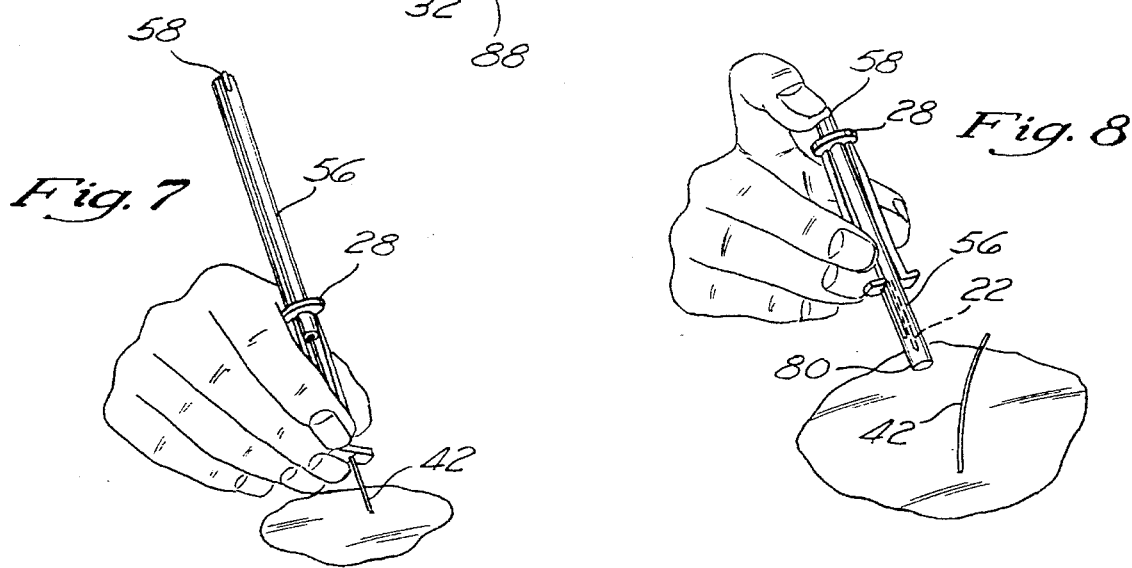
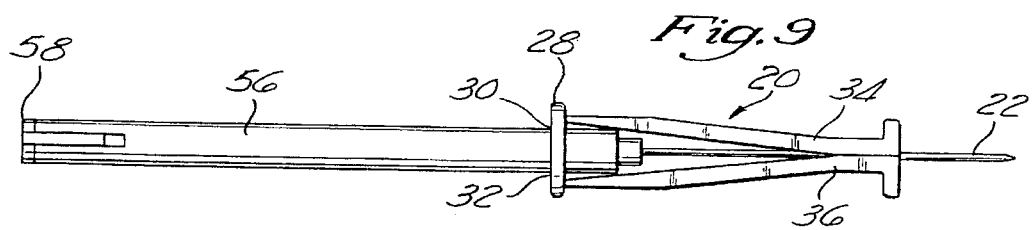
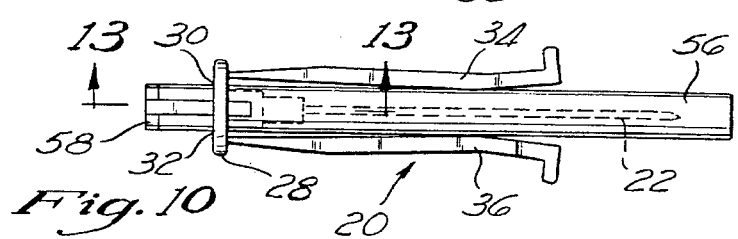

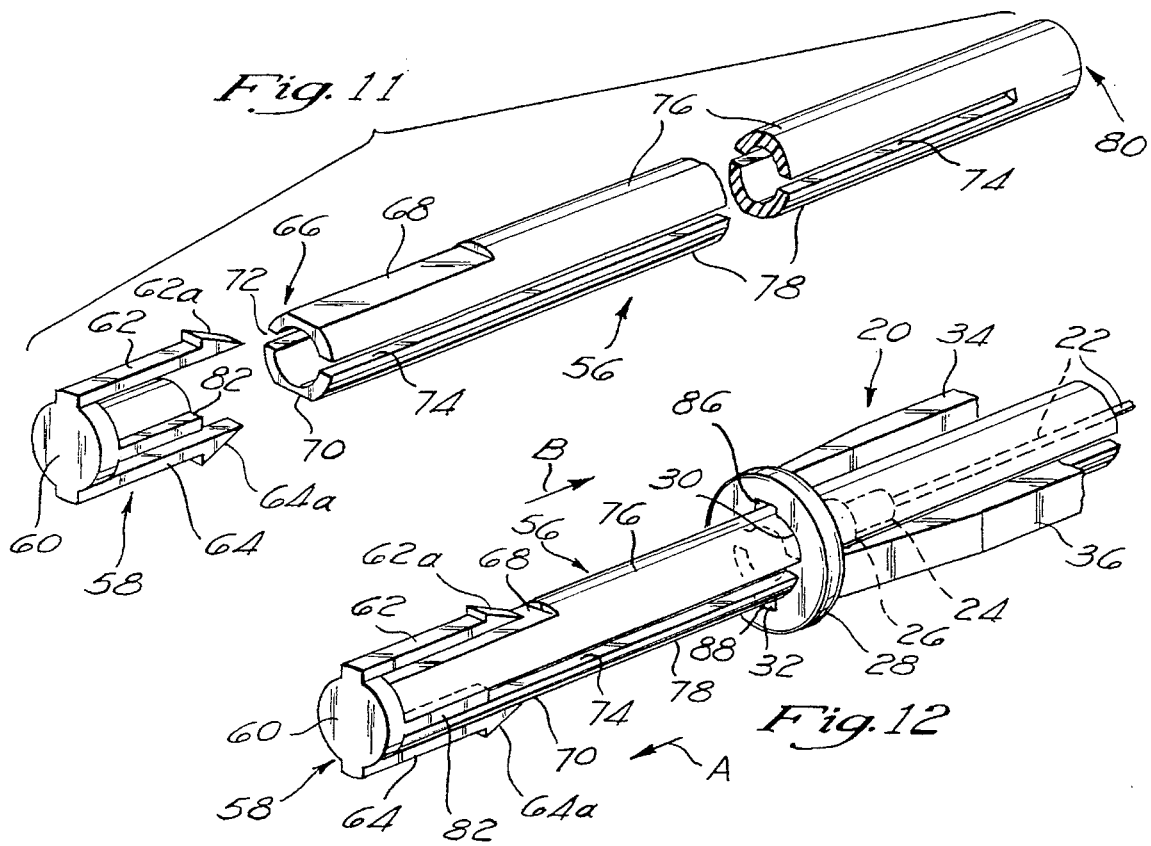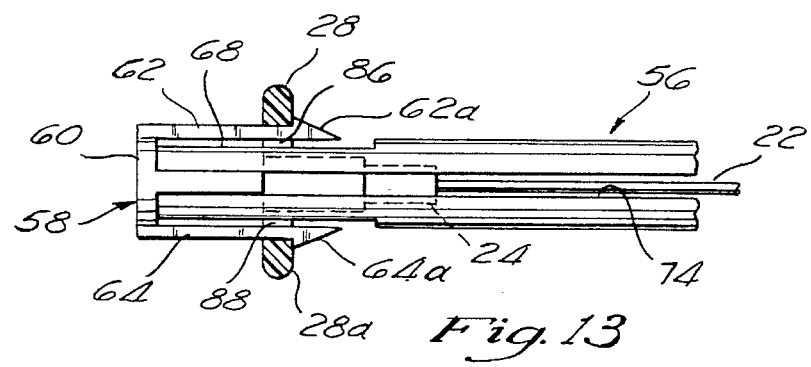

5,569,217

PERCUTANEOUS PORT CATHETER ASSEMBLY AND METHOD OF USE

This application is a division of application Ser. No. 08/144,881, filed Oct. 28, 1993, now U.S. Pat. No. 5,403,283.

FIELD OF THE INVENTION

The present invention relates to medical devices and methods for accessing surgically embedded drug delivery systems, both to reduce the wear on the embedded systems as well as to provide safer means for accessing the implanted systems.

BACKGROUND OF THE INVENTION

The use of surgically implanted ports as a means of enhancing drug delivery to desired patient locations is known. Typically, the port comprises a container that forms a reservoir with a resilient or rubberized septum on the access side nearest the skin and a rigid surface on a side opposite. The port also has an outlet tube through which any drugs or fluids that are deposited in the reservoir may flow outwardly to reach the desired organ or circulatory target. Physicians will frequently implant a port in an area to which the port can easily be accessed, and will frequently utilize the port for numerous drug administrations. The fact that the port is implanted is beneficial in that administered drugs will more selectively reach their target areas. Likewise, by being surgically implanted, accessing the port as opposed to directly administering drugs through a vein or other bodily tissue reduces the chance of the health practitioner of acquiring a blood-borne or other communicable disease.

However, certain problems exist with current devices and methods utilized to access surgically implanted ports. Usually a port is accessed by means of a catheter. The catheter is usually inserted into the septum by means of a hollow needle syringe that is received inside the catheter. Unfortunately, the use of a hollow needle causes coring in the septum and as a result, may cause the septum to leak medicines or other fluids intended to be targeted for other bodily areas. Consequently, the septum of the port becomes ineffective at retaining the drugs they are intended to hold, thus requiring more frequent drug administrations as well as premature replacement of the port.

Additional problems that can occur when trying to catheterize a surgically implanted port are the phenomenon of axial compaction and crimping. Axial compaction occurs when the catheter, while axially surrounding a needle, slides up the needle when the catheter and needle are inserted through soft tissue and into the septum of the port. The result of such compaction is that the catheter does not become fully inserted into fluid contact with the reservoir of the port and, as a result, fails in its intended purpose to administer drugs into the reservoir of the port. Crimping occurs when the catheter, once inserted, is bent to configure with the body of the patient. Conventional catheters, as a result of crimping, oftentimes become closed, thereby being incapable of allowing drugs or fluids to flow freely into the port and often must be replaced.

Still of further disadvantage of the current devices and methodology used to access ports is the risk involved to administering personnel with inadvertent needle-stick experiences. While the use of implanted ports is somewhat effective in limiting the amount of blood and tissue that is encountered while administering a drug through injection, a substantial risk is still present as the needles that are inserted into the septum do, in fact, come into contact with bodily fluids that may contain infective microbiological agents. More notably and commonly associated with these blood-borne diseases are AIDs and hepatitis B, which have the capability to infect an individual through such an inadvertent needle-stick experience. Accordingly, there is a need to minimize the risk that is involved for a potential needle-stick situation when inserting a catheter into such a surgically implanted port.

Not only is there a need to minimize the risk of a needle-stick experience, there is also a need for greater accuracy when inserting the needle and catheter into the septum. The traditional method of using a syringe axially surrounded within a catheter has the disadvantage of not providing the individual seeking to catheterize the port with any means of guiding and supporting the catheter into the port. As a result, problems can arise where the catheter and needle bend or deflect during insertion, thereby missing the port reservoir.

Attempts to remedy these problems have recently been made. U.S. Pat. No. 5,135,502 shows an apparatus for inserting a catheter within a surgically implanted port. The invention uses a solid stylet which is effective in preventing the coring of the septum of the port. Furthermore, the invention attempts to provide greater accuracy in inserting the needle and catheter into the implanted port as well as provide a means of preventing needle sticks upon retraction of the stylet. However, greater accuracy in inserting the needle and catheter as well as greater capability in preventing the risk of needle-stick experiences is still in need of further refinement.

Accordingly, there is a need to remedy the defects associated with the current methodology and devices used for catheterizing a surgically implanted port. Furthermore, there is a need to provide greater support and accuracy when inserting a catheter into a surgically implanted port as well as provide a more reliable means of enclosing the stylet upon retraction so as to prevent any risk of potential needle-stick experiences.

SUMMARY OF THE INVENTION

The present invention is directed to an apparatus and method for introducing a catheter into a septum of a surgically implanted port. The apparatus includes a catheter, a stylet connected to a housing with at least one member to protect the catheter and stylet when the two are interconnected, a casing, and a protective cap attached to one end of the casing. The stylet of the housing has a distal portion having a shaft and tip that is shaped and oriented so as to allow the catheter to slidably fit around the distal portion of the shaft of the styler. The housing connected to the stylet has at least one member that provides stability and support for the user of the apparatus when the stylet and catheter are interconnected in a fashion that is suitable for insertion into the septum. The supporting member, which can be in the form of flexible grips or holders, provides the stabilization and support when the member is manually manipulated or compressed about the interconnected catheter and stylet. Upon insertion of the catheter and stylet into the septum, the member for providing support and stabilization is disengaged by manually releasing the member or grips about the catheter and stylet. The casing with the fastened cap, which is slidably mounted within the housing, is depressed by means of pushing on the protective cap in such a manner that causes the casing to move through the housing and cause the distal end of the casing to simultaneously retract and encase the stylet while leaving the catheter embedded through the septum and in fluid communication with the reservoir of the port. The retracting and encasing occurs through the force of the advancing casing against the layer of tissue to which surrounds the septum of the port as the housing and connected stylet are moved in a direction opposite to the advancing casing.

The present invention is also directed to a method of introducing a catheter into a surgically implanted port. The method includes the steps of interconnecting a catheter and a stylet in a configuration that is suitable for insertion of both catheter and stylet into the septum of a port, the manipulation of an apparatus that stably introduces the catheter and stylet into the septum of the port, and retracting the stylet in a manner that protectively encases the stylet while leaving the catheter embedded within the port so as to remain in fluid communication.

In further embodiments of the apparatus, the protective cap has means for locking the casing into a fixed position upon depression of the protective cap into a segment of the housing so that the casing fully contains the retracted stylet in a way which prevents the stylet from potentially causing a needle-stick experience. In still further embodiments of the apparatus, both the stylet and catheter have preferable dimensions with respect to the diameter of the stylet and the diameter and wall thickness of the catheter. These dimensions are preferably within a 3-inch length for the stylet and within a 3-inch length for the catheter. The preferred embodiment contemplates 16 to 32 gauge for the stylet and 18 to 28 gauge for the catheter as being optimal. Moreover, the materials that are utilized to fabricate the catheter are (a polytetrafluoroethylene polymer, such as TEFLON, a registered trademark of Du Pont de Nemours, E.I., & Co., Inc.) or other thermoplastics, with the most preferable material being A polytetrafluoroethylene polymer, such as TEFLON. Of crucial importance to the present invention is the wall thickness and diameter of the catheter as well as the materials used for the catheter as these elements are quite advantageous in alleviating the problems associated with crimping.

With respect to the method, further embodiments include the use of preferred devices in carrying out the method. These preferred devices include a locking cap for carrying out the method in a way that locks a protective casing into a fixed position about a retracted stylet. In still further embodiments of the method, preferable dimensions concerning the diameter of the stylet as well as the diameter and wall thickness of the catheter are specified. Furthermore, materials concerning the composition of the catheter are also mentioned, which, most notably, include the use of polytetrafluoroethylene polymer, such as TEFLON.

The apparatus and method of the present invention is particularly advantageous in that both method and apparatus utilize a solid stylet for introducing the catheter into the port of the septum. By utilizing a solid stylet, the catheter becomes embedded within the port in a manner which does not cause coring of the septum as can occur with conventional prior art hollow needles as mentioned above. As a result, the septum has a longer life and can be utilized for a greater number of catheter insertions.

The present apparatus and method is of further advantage in that both apparatus and method utilize a housing having a member for stably guiding and supporting the interconnected catheter and stylet into the septum of the port. The member that is used for stably guiding and supporting the interconnected catheter and stylet, which is preferably in the form of a pair of flexible grips in juxtaposition, prevents the incidence of axial compaction of the catheter that can occur when the catheter slides up the stylet upon insertion of the catheter and stylet into the port of the septum. Furthermore, the member of stabilizing and supporting the interconnected catheter and stylet offers easier manipulation and accuracy as the member is oriented and shaped to directly target the intended injunction site and prevent any possible bending and/or lateral deflection of the stylet during insertion.

The present invention is of still further advantage in that the casing provides a greater degree of protection in preventing the possibility of an inadvertent needle-stick experience. The casing, which has a protective cap covering the proximal end of the casing, is slidably mounted within the housing and can be depressed so as to force the distal end of the casing to simultaneously retract and encase the stylet after insertion of both catheter and stylet into the septum of the port. The greater degree of protection arises through the action of the advancing distal end of the casing which is, at all times, being forced toward the injection site. Accordingly, the stylet at no time becomes exposed upon retraction and, because the force of the advancing distal end of the casing is moving towards the tissue, creates a systematic release that insures complete encasing of the stylet at all times during the retraction. Moreover, in a preferred embodiment, the protective cap of the proximal end of the casing has a spring-lock mechanism, which is preferably a pair of spring-lock panels, that lock into position once the cap has been sufficiently depressed into the housing. These spring-lock panels lock into place through grooves in orifice passages that are in the housing that, when in a locked position, maintain the casing in a locked position that fully encases the retracted stylet and maintains a protective configuration that greatly minimizes the risk of any potential needle stick. Once in this locked position, the casing and stylet may be discarded.

These and other features, aspects, and advantages of the present invention will become better understood with reference to the following description, appended claims, and accompanying drawings.

BRIEF DESCRIPTION OF THE DRAWING

FIG. 1 is a perspective view of a first embodiment of the present invention showing insertion of the stylet and catheter into an implanted port while being contained within a housing;

FIG. 2 is a perspective view of the catheter that has been placed in fluid communication with the port through the septum upon retraction of the stylet and housing;

FIG. 3 is a perspective view of the housing and styler with the stylet being axially surrounded by the catheter;

FIG. 4 is a perspective view of the housing an styler with the catheter in a disconnected condition;

FIG. 5 is a cross-sectional view of the catheter, stylet, and a portion of the housing taken along line 5—5 of FIG. 3;

FIG. 6 is a perspective view of the proximal end portion of the housing and stylet;

FIG. 7 is a perspective view of a second embodiment of the present invention showing the housing with a slidably mounted casing with protective cap being utilized to insert the catheter and stylet into an injection site;

FIG. 8 is a perspective view showing the device of FIG. 7 after retraction of the stylet from the inserted catheter;

FIG. 9 is a perspective view-of the housing and stylet with the casing and protective cap being slidably mounted therein;

FIG. 10 is a perspective view of the housing, stylet, and casing showing the encasement of the stylet after retraction of the stylet;

FIG. 11 is a perspective view of the protective cap with spring-lock members as it is placed and oriented with respect to the casing;

FIG. 12 is a perspective view of the housing and casing and protective cap as the casing is advanced to encase the stylet shown in broken lines; and FIG. 13 is a cross-sectional view of the protective cap while in a locked configuration with respect to the housing taken along line 13—13 of FIG. 10.

DETAILED DESCRIPTION OF THE PREFERRED EMBODIMENT

Referring to FIGS. 1 and 2, there is shown the percutaneous port catheter assembly of the present invention being utilized to insert a catheter 42 into the port 50. Such percutaneous ports 50 are well known in the art, one of which is disclosed in U.S. Pat. No. 5,135,502, the disclosure of which is expressly incorporated herein by reference. As is well known, the catheter is introduced through the soft tissue of the patient and through a septum 52 formed on the port. Once inserted into the septum, the introducer is removed from the catheter leaving one end of the catheter disposed within the internal reservoir of the port and the opposite end of the catheter available to subsequent connection to a conventional drug delivery system. As is typical, the length of the catheter 42 extending outside of the patient may be secured or stabilized to the patient via tape, as shown in FIG. 2.

The detailed construction of a first embodiment of the percutaneous port catheter introducer assembly of the present invention is shown generally in FIGS. 3-6 and 9-13. Referring to FIGS. 3 and 4, the introducer apparatus, hereinafter referred to as a housing 20 and stylet 22, is shown in accordance with the present invention. Also shown is catheter 42 having a sleeve 44 attached to its proximal end. With reference to FIG. 3, the catheter 42 is shown axially surrounding stylet 22 in a configuration suitable for injection into the septum of an implanted port. FIG. 4 depicts the catheter 42 in a disengaged state from the housing 20. As illustrated from these drawings, the catheter 42 with sleeve 44 is designed to axially surround stylet 22 with the sleeve of the catheter 44, which usually comprises a Luer lock being designed to receive protruding member 24 of the housing. Member 26 is designed to serve as a registry surface to support the catheter 42 once it has been securely and snugly placed over the stylet 22 with the sleeve of the catheter 44 being placed over member 24 of the housing.

The housing further includes a base 28 to which the members 26 and 24 are axially located with each member oriented toward the distal end of the stylet 22. The base further includes two passage orifices 30 and 32 (32 not shown), and two distally protruding members 34 and 36. In a preferred embodiment, members 34 and 36 are preferably in the configuration of elongate flexible grips in juxtaposition, having V-shaped grooves 38 and 40, whereupon manual compression or flexion of either side of the grips, as shown in FIG. 1, creates axial compression that supports and stabilizes the stylet 22 and catheter 42 when the stylet 22 and catheter 42 are injected through tissue and into the septum of a port. The frictional engagement that is provided by compressing the flexible grips over the interconnected catheter and stylet prevents the catheter from sliding up the stylet and insures better penetration of the catheter within the septum of the port.

Referring to FIG. 5, the catheter 42 and sleeve of the catheter 44 are shown in interconnected condition with the stylet 22 so that both stylet 22 and catheter 42 may be inserted into a surgically implanted port. As is illustrated, the sleeve of the catheter 44 interconnectibly engages member 24, with member 26 providing structure so as to support the catheter 42 and stylet 22 when the two are injected through the skin and into the port.

With the structure defined, the operation of the first embodiment of the present invention can be described with specific reference to FIGS. 1 and 2. When it is desired for administrative personnel to insert the catheter 42 into the percutaneous port 50, the practitioner positions the catheter 42 upon the length of the stylet 22 and seats the Luer lock fitting or hub 44 upon the registry member 24 of the introducer. Subsequently, the administrative personnel holds the introducer in his hand, preferably between the thumb and index finger as illustrated in FIG. 1. With the introducer held within the hand, the user compresses the elongate members 34 and 36 inwardly causing the members 34 and 36 to contact the outside diameter of the catheter 42. As will be recognized, during such contact, the catheter 42 and stylet 22 are maintained in proper axial registry by the plural V-shaped grooves 38 formed on the inner surfaces of the flexible members 34 and 36.

Subsequently, the administrative personnel may lower the introducer downward upon the patient and press the distal end of the stylet 22 and catheter 44 through the soft tissue of the patient and into the septum 52 of the port 50. During such axially downward movement, the length of the catheter 42 and stylet 22 is supported by engagement with the flexible members 34 and 36 thereby preventing any bending of the stylet and/or catheter during the insertion process. The stylet 22 and catheter 42 are then axially depressed through the septum 52 and into the internal reservoir of the port 50. As will be recognized, during such insertion of the catheter 42 and stylet 22 within the internal reservoir of he port 50, the engagement of the flexible members 34 and 36 with the catheter and stylet prevent any relative movement between the catheter 42 and stylet 22 and thereby deter any axial compaction of the catheter 42 along the length of the stylet 22. Subsequently, the administrative personnel releases the compressive force exerted upon the flexible members 34 and 36 and manually withdraws the introducer outwardly from the port. Due to the resilient nature of the septum 52, frictional forces exerted upon the distal tip of the catheter 42 cause the catheter 42 to be retained within the reservoir 50 and the inducer and stylet 22 may be completely removed from the catheter and subsequently discarded. The administrative personnel may then secure the catheter 42 to the soft tissue of the patient via a conventional tape strip and the Luer lock fitting 44 of the catheter may then be connected to conventional drug-administering apparatus to allow drugs to pass through the catheter 42 and into the port 50.

Referring to FIGS. 7-13, a second embodiment of the present invention is depicted which functions in an analogous manner to the first embodiment of the present invention but additionally includes an elongate casing or sheath 56 which is reciprocally mounted upon the introducer to prevent inadvertent needle sticks to administrating personnel.

As shown, a protective casing 56 is slidably mounted within the housing 20. The casing 56 is mounted in such a way that allows the casing 56 to pass axially through the passage orifices 30 and 32 of base 28, as depicted in FIG. 10. At the proximal end of casing 56 is a protective cap 58, which covers the proximal end of the casing 56.

FIG. 9 further depicts a first position of the second embodiment utilizing the casing 56, wherein the casing is withdrawn toward the proximal end of the housing. With the casing 56 in this configuration, the housing may be utilized to insert a catheter into a port, as discussed above. However, when the user pushes the fastened protective cap 58, the casing 56 is pushed through the housing 20 so as to fully encase the stylet 22. Furthermore, through the housing 20, the flexible grips 34 and 36 are pushed away from the stylet so that the user can no longer apply axial compression to the stylet 22 and catheter 42. By removing the axial support and frictional engagement provided by the flexible grips 36 and 34, the stylet 22 may be then retracted in a manner that leaves the catheter 42 embedded in within the port. Illustrative of this illustration is FIG. 10 wherein the casing 56 has been sufficiently pushed so as to fully encase the stylet 22 as well as cause a separation of each flexible grip, 34 and 36, respectively.

In relation to the casing utilized in the preferred embodiment, a perspective view of both the casing 56 and the protective cap 58 that is carried at the proximal end of the casing is depicted in FIG. 11. The protective cap has an outer surface 60 which is used to depress the casing 56 through the housing 20 and stylet 22. The protective cap 58, in a preferred embodiment, included one or more spring-lock members or panels 62 and 64 which are to be received upon surfaces 68 and 70 of the casing 56. Side panels, such as 82, are further included so as to provide a surface to attach to casing 56 by snugly fitting within grooves 72 and 74.

The distal end 80 of the casing 56 has a barrel section which advantageously serves as a base for retracting the inserted stylet. From this distal end of the casing 56 protrude members 76 and 78, which are in juxtaposition and are separated by passages 72 and 74.

With reference to FIG. 12, casing 56 is shown slidably mounted within the housing 20. Members 76 and 78 are received through passage orifices 30 and 32. In use, members 76 and 78 of the proximal end are inserted through the passage orifices 30 and 32 so that the protective cap 58 may be fastened to the proximate end of the casing 56. Once slidably mounted within the housing, the protective cap may be fastened whereby a panel, such as 82, is inserted through slots, such as 74. Furthermore, the spring-lock panels 62 and 64 are further placed upon receiving panels and 70 and 68. It should be noted that the passage orifices 30 and 32 also have a void to except the spring-lock panels 62 and 64 and are designed with recesses to receive and lock the spring panels 62 and 64 into place once the protective cap 58 is pushed sufficiently far into the passage orifices 30 and 32 of base 28.

FIG. 13 represents the configuration where the protective cap 58 is engaged in a locked position with the housing 20. Spring panels 62 and 64 become lodged within the base 28 of the housing 20 so that the panels 62 and 64 become fixed in place so that the protective cap 58 and its connected casing 56 remain in a state that prevents the cap 58 or casing 56 to be retracted. The overall effect is to fix the casing 56 in a position with respect to housing 20 so that the stylet 22, upon retraction, cannot be exposed so as to reduce the risk of causing a needle-stick experience.

FIGS. 7 and 8 illustrate the use of the second preferred embodiment of the present invention. In use, the manual manipulation of the flexible grips provide axial compression and frictional engagement so as to accurately and forcefully insert the stylet 22 and catheter 42 through a layer of tissue into the septum of a port. As shown, the casing 56 with protective cap 58 are in a fully retracted position so that the distal end of the casing abuts the base 28 of the housing 20. Accordingly, there is no interference with use of the flexible grips used to insert the catheter into the port.

Once the catheter has been sufficiently embedded within the port, the stylet is retracted in a safe manner. FIG. 8 depicts such advantageous retraction as the protective casing 56 fully encases the retracted stylet while leaving the previously interconnected catheter 42 sufficiently embedded within a port. This retraction is essentially carried out by depressing the protective cap 58 so as to cause the slidably mounted casing 56 to move towards the distal end of the stylet 22, so that the distal end of the casing 56 separates the flexible grips so as to release the axial compression that had previously kept the catheter 42 and stylet 22 in an interconnected configuration. Simultaneously, the distal end of the casing 56 further encases the stylet 22 as well as cause the retraction of the stylet 22 with the result being the safe and secure catheterization of the port.

Referring now to FIG. 11, perspectively illustrated is the casing 56 of the present invention and protective cap 58 which is releasably fastened to the proximal end 66 of the casing 56. In the preferred embodiment, one end of the protective cap 58 defines a circularly configured outer surface 60 to which pressure may be applied for purposes of forcing the casing 56 through the housing 20. The opposed pair of spring-lock panels 62, 64 are extensible over a pair of corresponding, generally planar surfaces 68, 70 formed within the casing 56 adjacent the proximal end 59 thereof. The protective cap 58 further defines a pair of side panels 82, 84 which are slidably receivable into an opposed pair of elongate grooves 72, 74 disposed within the proximal end 66 of the casing 56 and extending longitudinally through a substantial portion of the length thereof. In this respect, the longitudinal extension of the grooves 72, 74 through the casing 56 substantially bisects the same into an identically configured, juxtaposed pair of casing portions 76, 78. As further seen in FIG. 11, the distal end 80 of the casing 56 defines a barrel section which is utilized as a base for retracting the inserted stylet 22.

Referring now to FIG. 12, prior to the attachment of the protective cap 58 to the casing 56, the proximal end 66 of the casing 56, and more particularly the casing portions 76, 78, are slidably extended through respective ones of the passage orifices 30, 32 in the direction designated by the arrow A. Subsequent to the extension of the casing portions 76, 78 through the passage orifices 30, 32, the protective cap 58 is fastened to the proximal end 59 of the casing 56 in the manner previously described. Thereafter, pressure is applied to the outer surface 60 of the protective cap 58 thus facilitating the sliding movement of is the casing portions 76, 78 axially through the passage orifices 30, 32 in the direction designated by the arrow B. As will be recognized, the passage of the casing 56 through the passage orifices 30, 32 in the direction B is limited by the engagement of the protective cap 58 to the base 28, as seen in FIG. 13.

Referring now to FIG. 13, the engagement of the protective cap 58 to the base 28, and thus the housing 20, is facilitated by the extension of the spring-lock panels 62, 64 through a pair of recesses 86 and 88 which are defined within the base 28 and communicate with the passage orifices 30, 32. In particular, when the casing 56 is extended into the housing 20 in the direction B, the beveled surfaces 62a, 64a defined on the distal tips of the spring-lock panels 62, 64 are brought into abutting contact with the lower edges of respective ones of the recesses 86 and 86 thus forcing or flexing the spring-lock panels 62, 64 inwardly. After the beveled surfaces 62a, 64a are extended completely through the recesses 86 and 88, the spring-lock panels 62, 64 return to their original, un-flexed orientation, with portions of the spring-lock panels 62, 64 residing within the recesses 86 and 88 and being abutted against the distal surface 28a of the base 28. Importantly, the outward biasing force exerted by the spring-lock panels 62, 64 within the recesses 86 and 88 locks or lodges the same within the base 28 of the housing 20, thus fixing the protective cap 58 therewithin and preventing the protective cap 58 or casing 56 from being retracted from within the base 28 in the direction A. Advantageously, by maintaining the casing 56 in a locked orientation within the housing 20, the stylet 22, upon retraction, cannot be exposed, thus reducing the risk of needle-sticks.

In both preferred embodiment of both apparatus and method, both the stylet 22 and the catheter 42 should have dimensions that compliment one another so as to insure a snug fit that enables both catheter 42 and stylet 22 to be inserted within a port. Preferably, the stylet should have a diameter that falls within the ranges of 0.015 inch and 0.080 inch, the most preferable diameter being 0.020 inch. Likewise, the catheter should also have a diameter falling within the ranges of 0.012-inch inside diameter to 0.060-inch inside diameter with an inner optimal diameter being 0.020 inch. Also of great importance to several of the preferred embodiments of the present invention is the wall thickness of the catheter. The wall thickness of the catheter is extremely crucial to insure greater stability upon injection as well as providing a better means through which to access the port. Accordingly, an optimal catheter wall thickness should fall within the ranges of 0.004 inch to 0.012 inch, with the most optimal wall thickness being 0.070 inch.

Furthermore, the materials used to practice the present invention are of great importance. With respect to the stylet, a most suitable material may include one of the following: tungsten or stainless steel, with a most preferred material being 316 stainless steel. The catheter may be made of materials that can be selected from thermoplastics, with a polytetrafluoroethylene polymer, such as TEFLON being the most preferred material. Catheters made of a polytetrafluoroethylene polymer, such as TEFLON are advantageous in that a polytetrafluoroethylene polymer, such as TEFLON has radial and longitudinal compressive strength that prevents the septum of the port from causing the catheter to collapse once inserted into the port. Furthermore, the use of a polytetrafluoroethylene polymer, such as TEFLON is advantageous as it allows bending without kinking once inserted within the septum of the port. Materials that are to be used to construct the housing, casing, or protective cap may be selected from various materials including any stiff thermoplastics, all of which should be suitable for practicing the present invention.

Thus, the apparatus of the present invention, with the various preferred embodiments thereof, as well as the preferred method of using the present invention, have been described in detail with the various advantages of both apparatus and method being set forth. It is understood, however, that equivalents are possible and that variations in structure may be made that fall within the underlying principles of the present invention.

What is claimed is:

1. An apparatus for introducing a catheter into a septum of a surgically implanted port comprising:

a) a catheter for accessing the port, wherein the catheter is comprised of a polytetrafluorethylene polymer;

b) a solid stylet;

c) a housing for securing the stylet within the catheter so that the catheter and styler are maintained in a slidably interconnectible configuration, the housing having at least one member for stably guiding and supporting the interconnected catheter and stylet through the septum of the port;

d) a asking with proximal and distal end portions slidably mounted within the housing, the distal end portion being oriented and designed to simultaneously encase and force the retraction of the stylet, the proximal end portion extending beyond a portion of the housing;

e) a cap fastened to the proximal end portion of the casing, the cap being so connected, that, when depressed, forces the entire length of the casing to advance a distance sufficient to fully retract and encase the styler while permitting the interconnected catheter to disengage from the styler and remain sufficiently embedded within the port;

f) wherein the stylet is internally fastened within the housing;

g) wherein the catheter comprises a tube of flexible material forming distal end proximal end portions, the proximal end portion being connected to a sleeve;

h) wherein the stylet comprises distal and proximal end portions, the distal portion having a shaft and tip, the shaft being shaped and oriented to slidably fit longitudinally within the catheter in a configuration suitable for insertion of both the catheter and the stylet into the septum of the port;

i) wherein the housing comprises a base securely fastened to the proximal end portion of the stylet, the base having at least one passage orifice, the base having a first member protruding axially about the styler toward the distal end of the stylet, the first member being shaped and oriented so as to be received in reversible engagement with the sleeve of the proximal end of the catheter, the base having at least one second member oriented toward the distal end portion of the styler, the second member being shaped and oriented so as to stably hold the catheter and the stylet while the catheter and stylet are in a longitudinally interconnectible configuration suitable for insertion into the septum of the port;

j) wherein the casing comprises a barrel section end portion having at least one member projecting longitudinally from the barrel section so as to form the proximal end portion, the member being designed to be received in the passage orifice and extending longitudinally beyond the housing;

k) wherein the cap comprises an apparatus for fastening the cap to the proximal end portion of the casing, the protective cap having an outer surface that, when depressed, forces the casing to longitudinally advance through the housing toward the distal end of the stylet so that the distal end portion of the casing simultaneously retracts and protectively encases the styler while leaving the catheter embedded within the septum of the port at a depth sufficient to allow for fluid communication between the distal end of the catheter and the reservoir of the port;

l) wherein the base of the housing has two passage orifices, the orifices each having a slot for receiving spring-lock panels;

m) wherein the second member of the base for stably guiding and supporting the interconnected catheter and styler are flexible grips in juxtaposition, the flexible grips each having a slot that, when manually compressed, provides axial support for the interconnected catheter and stylet and provides a structure for applying force to insert the interconnected catheter and styler into the septum of the port;

n) wherein the casing having two proximately projecting members, each member being received in a separate passage orifice; and o) wherein the cap further comprises two spring-lock panels that descend towards the distal end of the casing that lock the casing into position when the spring-lock panels are compressed into the slots or receiving the spring-lock panels, the slots defining a portion of the passage orifices.

2. The apparatus of claim 1 wherein:

a) the stylet is internally fastened within the housing;

b) the base of the housing has two passage orifices, the orifices each having a slot for receiving spring-lock panels;

c) the second member of the base for stably guiding and supporting the interconnected catheter and stylet are flexible grips in juxtaposition, the flexible grips each having a slot that, when manually compressed, provides axial support for the interconnected catheter and stylet and provides a structure for applying force to insert the interconnected catheter and stylet into the septum of the port;

d) the casing having two proximately projecting members, each member being received in a separate passage orifice; and e) the cap further comprises two spring-lock panels that descend towards the distal end of the casing that lock the casing into position when the spring-lock panels are compressed into the slots for receiving the spring-lock panels, the slots defining a portion of the passage orifices.

3. The apparatus of claim 2 wherein the catheter has an inside diameter of substantially 0.012 inch to 0.060 inch, and a length of substantially 1 inch to 6 inches.

4. A method of catheterizing a septum of a surgically implanted port comprising the steps of:

a) providing a catheter for accessing the port, a solid stylet attached to a housing having at least one member for stably guiding and supporting the catheter and stylet when the catheter and stylet are in an interconnected configuration suitable for inserting both stylet and catheter into the septum of the port, a casing with proximal and distal end portions being slidably mounted within a portion of the housing, and a cap fastened to the proximal end portion of the casing;

b) slidably interconnecting the catheter around the stylet so that the catheter and stylet are in a reversibly engaging configuration suitable for insertion of both stylet and catheter into the septum of the port;

c) manipulating the member for stably guiding and supporting the interconnected catheter and stylet so that the interconnected catheter and stylet are axially stabilized and immobilized;

d) applying sufficient force to the member for stably guiding and supporting the interconnected catheter and stylet penetrate the septum and remain embedded therein;

e) disengaging the member for stably guiding and supporting the interconnected catheter and stylet;

f) depressing the cap attached to the proximal end portion of the casing with sufficient force to cause the casing to move through the housing so that the distal end portion of a casing simultaneously retracts and protectively encases the stylet;

g) wherein the catheter comprises a tube of flexible material forming distal and proximal end portions, the proximal end portion being connected to a sleeve;

h) wherein the stylet comprises distal and proximal end portions, the distal portion having a shaft and tip, the shaft being shaped and oriented to slidably fit longitudinally within the catheter in a configuration suitable for insertion of both the catheter and the stylet into the septum of the port;

i) wherein the housing comprises a base securely fastened to the proximal end portion of the stylet, the base having at least one passage orifice, the base having a first member protruding axially about the stylet toward the distal end of the stylet, the first member being shaped and oriented so as to be received in reversible engagement with the sleeve of the proximal end of the catheter, the base having at least one second member oriented toward the distal end portion of the stylet, the second member being shaped and oriented so as to stably hold the catheter and the stylet while the catheter and stylet are in a longitudinally interconnectible configuration suitable for insertion into the septum of the port;

j) wherein the casing comprises a barrel section end portion having at least one member projecting longitudinally from the barrel section so as to form the proximal end portion, the member being designed to be received in the passage orifice and extending longitudinally beyond the housing;

k) wherein the cap further comprising an apparatus for fastening the cap to the proximal end portion of the casing, the cap having an outer surface that, when depressed, forces the casing to longitudinally advance through the housing toward the distal end of the stylet so that the distal end portion of the casing simultaneously retracts and protectively encases the stylet while leaving the catheter embedded within the septum of the port at a depth sufficient to allow for fluid communication between the distal end of the catheter and the reservoir of the port;

l) wherein the base of the housing has two passage orifices, the orifices each having a slot for receiving spring-lock panels;

m) wherein the second member of the base for stably guiding and supporting the interconnected catheter and stylet are flexible grips in juxtaposition, the flexible grips each having a slot that, when manually compressed, provides axial support for the interconnected catheter and stylet and provides a structure for applying force to insert the interconnected catheter and stylet into the septum of the port; and n) wherein the cap further comprises two spring-lock panels that descend towards the distal end of the casing that lock the casing into position when the spring-lock panels are compressed into the slots for receiving the spring-lock panels connected to the base of the housing.

5. The method of claim 4 wherein the catheter has an inside diameter within the range of 0.012 to 0.060 inch and a length within the range of 1 inch to 6 inches.

6. A method of catheterizing a septum of a surgically implanted port comprising the steps of:

a) providing a catheter for accessing the port, a solid stylet attached to a housing having at least one member for stably guiding and supporting the catheter and stylet when the catheter and stylet are in an interconnected configuration suitable for inserting both stylet and catheter into the septum of the port, a casing with proximal and distal end portions being slidably mounted within a portion of the housing, and a cap fastened to the proximal end portion of the casing;

b) slidably interconnecting the catheter around the stylet so that the catheter and stylet are in a reversibly engaging configuration suitable for insertion of both stylet and catheter into the septum of the port;

c) manipulating the member for stably guiding and supporting the interconnected catheter and stylet so that the interconnected catheter and stylet are axially stabilized and immobilized;

d) applying sufficient force to the member for stably guiding and supporting the interconnected catheter and stylet penetrate the septum and remain embedded therein;

e) disengaging the member for stably guiding and supporting the interconnected catheter and stylet;

f) depressing the cap attached to the proximal end portion of the casing with sufficient force to cause the casing to move through the housing so that the distal end portion of a casing simultaneously retracts and protectively encases the stylet;

g) wherein the catheter comprises a tube of flexible material forming distal and proximal end portions, the proximal end portion being connected to a sleeve;

h) wherein the stylet comprises distal and proximal end portions, the distal portion having a shaft and tip, the shaft being shaped and oriented to slidably fit longitudinally within the catheter in a configuration suitable for insertion of both the catheter and the stylet into the septum of the port;

i) wherein the housing comprises a base securely fastened to the proximal end portion of the stylet, the base having at least one passage orifice, the base having a first member protruding axially about the stylet toward the distal end of the stylet, the first member being shaped and oriented so as to be received in reversible engagement with the sleeve of the proximal end of the catheter, the base having at least one second member oriented toward the distal end portion of the stylet, the second member being shaped and oriented so as to stably hold the catheter and the stylet while the catheter and stylet are in a longitudinally interconnectible configuration suitable for insertion into the septum of the port;

j) wherein the casing comprises a barrel section end portion having at least one member projecting longitudinally from the barrel section so as to form the proximal end portion, the member being designed to be received in the passage orifice and extending longitudinally beyond the housing;

k) wherein the cap further comprises an apparatus for fastening the cap to the proximal end portion of the casing, the cap having an outer surface that, when depressed, forces the casing to longitudinally advance through the housing toward the distal end of the stylet so that the distal end portion of the casing simultaneously retracts and protectively encases the stylet while leaving the catheter embedded within the septum of the port at a depth sufficient to allow for fluid communication between the distal end of the catheter and the reservoir of the port;

l) wherein the stylet is internally fastened within the housing;

m) wherein the base of the housing has two passage orifices, the orifices each having a slot for receiving spring-lock panels;

n) wherein the second member of the base for stably guiding and supporting the interconnected catheter and stylet are flexible grips in juxtaposition, the flexible grips each having a slot that, when manually compressed, provides axial support for the interconnected catheter and stylet and provides a structure for applying force to insert the interconnected catheter and stylet into the septum of the port;

o) wherein the casing has two proximately projecting members, each member being received in a separate passage orifice; and p) wherein the cap further comprises two spring-lock panels that descend towards the distal end of the casing that lock the casing into position when the spring-lock panels are compressed into the slots for receiving the spring-lock panels, the slots defining a portion of the passage orifices.

7. A method of catheterizing a septum of a surgically implanted port comprising the steps of:

a) providing a catheter for accessing the port, a solid stylet attached to a housing having at least one member for stably guiding and supporting the catheter and styler when the catheter and stylet are in an interconnected configuration suitable for inserting both stylet and catheter into the septum of the port, a casing with proximal and distal end portions being slidably mounted within a portion of the housing, and a cap fastened to the proximal end portion of the casing;

b) slidably interconnecting the catheter around the stylet so that the catheter and stylet are in a reversibly engaging configuration suitable for insertion of both styler and catheter into the septum of the port;

c) manipulating the member for stably guiding and supporting the interconnected catheter and stylet so that the interconnected catheter and stylet are axially stabilized and immobilized;

d) applying sufficient force to the member for stably guiding and supporting the interconnected catheter and stylet penetrate the septum and remain embedded therein;

e) disengaging the member for stably guiding and supporting the interconnected catheter and stylet;

f) depressing the cap attached to the proximal end portion of the casing with sufficient force to cause the casing to move through the housing so that the distal end portion of a casing simultaneously retracts and protectively encases the stylet;

g) wherein the catheter comprises a tube of flexible material forming distal and proximal end portions, the proximal end portion being connected to a sleeve;

h) wherein the styler comprises distal and proximal end portions, the distal portion having a shaft and tip, the shaft being shaped and oriented to slidably fit longitudinally within the catheter in a configuration suitable for insertion of both the catheter and the stylet into the septum of the port;

i) wherein the housing comprises a base securely fastened to the proximal end portion of the stylet, the base having at least one passage orifice, the base having a first member protruding axially about the stylet toward the distal end of the stylet, the first member being shaped and oriented so as to be received in reversible engagement with the sleeve of the proximal end of the catheter, the base having at least one second ember oriented toward the distal end portion of the stylet, the second member being shaped and oriented so as to stably hold the catheter and the stylet while the catheter and stylet are in a longitudinally interconnectible configuration suitable for insertion into the septum of the port;

j) wherein the casing comprises a barrel section end portion having at least one member projecting longitudinally from the barrel section so as to form the proximal end portion, the member being designed to be received in the passage orifice and extending longitudinally beyond the housing;

k) wherein the cap further comprises an apparatus for fastening the cap to the proximal end portion of the casing, the protective cap having an outer surface that, when depressed, forces the casing to longitudinally advance through the housing toward the distal end of the stylet so that the distal end portion of the casing simultaneously retracts and protectively encases the stylet while leaving the catheter embedded within the septum of the port at a depth sufficient to allow for fluid communication between the distal end of the catheter and the reservoir of the port l) wherein the catheter is comprised of a polytetrafluoroethylene polymer;

m) wherein the stylet is internally fastened within the housing;

n) wherein the base of the housing has two passage orifices, the orifices each having a slot for receiving spring-lock panels;

o) wherein the second member of the base for stably guiding and supporting the interconnected catheter and stylet are flexible grips in juxtaposition, the flexible grips each having a slot that, when manually compressed, provides axial support for the interconnected catheter and styler and provides a structure for applying force to insert the interconnected catheter and stylet into the septum of the port;

p) wherein the casing having two proximately projecting members, each member being received in a separate passage orifice; and q) wherein the cap further comprises two spring-lock panels that descend towards the distal end of the casing that lock the casing into position when the spring-lock panels are compressed into the slots for receiving the spring-lock panels, the slots defining a portion of the passage orifices.

* * * * *